US00PP23794P2

(12) United States Plant Patent
Kordes

(10) Patent No.: US PP23,794 P2
(45) Date of Patent: Aug. 6, 2013

(54) MINIATURE ROSE PLANT NAMED 'KORPOT008'

(50) Latin Name: *Rosa hybrida*
Varietal Denomination: KORpot008

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 44 days.

(21) Appl. No.: 13/385,355

(22) Filed: Feb. 14, 2012

(51) Int. Cl.
*A01H 5/00* (2006.01)

(52) U.S. Cl.
USPC ..... Plt./121; Plt./120

(58) Field of Classification Search
USPC ..... Plt./121
See application file for complete search history.

(56) References Cited

U.S. PATENT DOCUMENTS

PP19,754 P3 * 2/2009 Jauchen ..... Plt./121

* cited by examiner

*Primary Examiner* — Wendy C Haas

(57) ABSTRACT

A new and distinct variety of rose with long lasting, novel pink flowers, and attractive foliage with very good disease resistance. It exhibits moderate vigor with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot008'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1998. The crossing was between an 'un-named seedling', the seed parent; and another 'un-named seedling' (both unpatented), the pollen parent, from the same inventor.

The resulting seeds were planted during the following winter, and they germinated and grew in the early spring. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot008'.

SUMMARY OF THE INVENTION

The new rose plant may be distinguished from its seed parent, an 'un-named seedling', by the following combination of characteristics:

1. 'KORpot008' has medium sized pink flowers, whereas the seed parent has large purple colored flowers.

2. 'KORpot008' has a compact growth habit, whereas the seed parent has an upright growth habit.

The new rose plant may be distinguished from its pollen parent, an 'un-named seedling', by the following combination of characteristics:

1. 'KORpot008' has medium pink flowers with a double petal count, whereas the pollen parent has cream white flowers with a very double petal count.
2. 'KORpot008' has a very good shelf life, whereas the pollen parent has an excellent shelf life.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot008' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot008' was selected in June, 1999 from the seedling beds to be asexually propagated for further evaluation. The first asexual propagation of 'KORpot008' was done in June, 1999 by taking and rooting cuttings at the inventor's nursery in Offenseth-Sparrieshoop, Germany.

This initial and other subsequent propagations conducted in controlled environments demonstrate that 'KORpot008' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpot008'.

DETAILED BOTANICAL DESCRIPTION

The following is a description of 'KORpot008', as observed growing in September, 2011 in a nursery in Jackson County, Oreg. on plants 8 months of age. Color references are made using The Royal Horticultural Society (London, England) Colour Chart, 2001 except where common terms of color are used.

For a comparison, several physical characteristics of the rose variety 'KORpagbel', a rose variety from the same inventor described and illustrated in U.S. Plant Pat. No. 17,183 and issued on Nov. 7, 2006 are compared to 'KORpot008' in Chart 1.

CHART 1

| Characteristic | 'KORpot008' | 'KORpagbel' |
|---|---|---|
| Bud color | Red Group 49A | Red Group 36A |
| Petals, average range | 50-55 | 40-45 |
| Petaloids | 25-35 | 8-10 |

Parents:

*Seed parent*.—'Un-named seedling'.

*Pollen parent*.—'Un-named seedling'.

Classification:

*Botanical classification*.—*Rosa hybrida* 'KORpot008'.

*Commercial classification*.—Miniature rose.

FLOWER AND FLOWER BUD

Blooming habit: Continuous.

Flower bud:

*Size*.—Upon opening, 30 mm in length from base of receptacle to distal end of bud and 15 mm diameter at its widest point.

*Bud form*.—Short. Pointed ovoid.

*Bud color*.—As sepals first unfold, bud color is Red Group 49A. When ¼ open, the upper surface of petals is Red Group 37D, and the lower surface is Red Group 49B.

*Sepals*.—Color: Upper surface Green Group 137C. Lower surface Green Group 137D. Size: Average 30-35 mm (l)×7 mm (w). Shape: Strong foliaceous appendages on 3 of the five sepals. Apex: cirrose. Base: Flat at union with receptacle. Quantity: Five. Surface texture: Upper side: Moderately pubescent. Lower surface: Moderately pubescent. Stipitate glands: Observed on margins and occasionally on upper and lower sides.

Receptacle:

*Surface*.—With small, fine white hairs.

*Color*.—Yellow-Green Group 144B.

*Shape*.—Funnel.

*Size*.—10 mm (h)×7-8 mm (w).

Peduncle:

*Surface*.—With fine hairs and stipitate glands.

*Length*.—30 to 35 mm average length.

*Diameter*.—3 mm average diameter.

*Color*.—Yellow-Green Group 144A.

*Strength*.—Strong.

*Borne*.—The number of buds per stem ranges from 1 to 5.

Flower bloom:

*Fragrance*.—None to a light sweet fragrance.

*Duration*.—On the plant approximately 21 days. Long lasting. As a cut flower, 7 to 8 days. Senesced petals drop away cleanly.

*Size*.—Large for a pot rose. When open, the average flower diameter is 70 mm and the average flower height is 30 mm.

*Form*.—Shape of flower when viewed from the side: Upon opening, upper part: Flattened convex. Upon opening, lower part: Flattened convex. Open flower, upper part: Flat. Open flower, lower part: Flattened convex.

Color:

*Upon opening, petals*.—Outermost petals: Outer Side: Red Group 49A and 49B. Inner Side: Red Group 52D. Innermost petals: Outer Side: Red Group 49B. Inner Side: Red Group 52D.

*Upon opening, basal petal spots*.—Basal petal spot, outermost petals: Outer Side: Yellow-Green Group 150D. Inner Side: Yellow-Green Group 150D. Basal petal spot, innermost petals: Outer Side: Green-Yellow Group 1B and 1C. Inner Side: Green-Yellow Group 1A and 1B.

*After opening, petals*.—Outermost petals: Outer Side: Red Group 52D, with a marginal zone of Red Group 49B and 49C and a small vertical stripe of Yellow-Green Group 150D. Inner Side: Red Group 49D. White venation present on many of the outermost petals. Innermost petals: Outer Side: Red Group 52D. Inner Side: Red Group 52D.

*After opening, basal petal spots*.—Basal petal spot, outermost petals: Outer Side: Yellow-Green Group 150D. Inner Side: Green-Yellow Group 1D. Basal petal spot, innermost petals: Outer Side: Yellow Group 2B. Inner Side Yellow Group 2A.

General tonality: On open flower: Red Group 49A.

Petals:

*Petal count*.—Very double.

*Average range*.—Approximately 50-55 petals under normal conditions.

*Petal reflex*.—Petals reflex strongly.

*Petal edge*.—With point in center of margin.

*Petal shape*.—Obovate. Apex shape is round. Shape of base is rounded.

*Petal size*.—25-35 mm (l) 10-15 mm (w).

*Thickness*.—Thick.

*Petal arrangement*.—Formal.

Petaloids:

*Petaloid count*.—Average of 25-35 per flower.

*Petaloid size*.—Petaloids are 10-15 mm (l) and 7-12 mm (w).

*Petaloid color*.—Color of inner side is Red Group 43D. Color of outer side is Red Group 43C.

*Petaloid texture*.—Thick.

*Margins*.—Undulated.

*Petaloid shape*.—Most commonly deltoid, with some petaloids highly irregular. Apex: Deltoid. Base: Pointed.

Reproductive organs:

*Pistils*.—Approximately 30 present. Stigmas: Location: Slightly inferior in position to anthers. Color: Green-Yellow Group 1C and 1D. Styles: Length: About 9 mm long. Color: Green-White Group 157C, with Red-Purple Group 60D intonations on top of style before the stigma.

*Stamens*.—Approximately 30 on average and regularly arranged. Anthers: Size: Average 3 mm long. Pollen: Very limited pollen present. Color: Yellow Group 13A and 13B. Filaments: Color: Yellow Group 4B. Length: 2-5 mm.

THE PLANT

Growth: Moderate growth.

Plant habit: Compact, bushy habit. When grown as a 15 cm pot plant, the average plant height is 25-30 cm and the average plant width is 18-22 cm.

Stems:

*Stem color*.—Young wood: Green Group 143C. Older wood: Green Group 138A.

*Stem surface*.—Young wood: Smooth. Older wood: Smooth.

Prickles: Present.

*Incidence*.—Average of 15-20 per each 10 cm of stem.

*Size*.—Average length: 5 mm.

*Color*.—Immature prickles: Greyed Red Group 182B and 182C. Mature prickles: Greyed-Orange Group 166A. Senescing to Grey-Brown Group N199C. Slight intonations: Greyed Red Group 182A.

*Shape*.—Concave.

Leaves and leaflets: Normally 5 leaflets on normal leaves in middle of the stem.

*Venation pattern*.—Pyramidal net pattern.

*Leaf size*.—75-80 mm (l)×55-60 mm (w).

*Abundance*.—Abundant Foliage.

*Texture*.—Leathery. Upper side of leaflet: Semi-glossy, smooth. Under side of leaflet: Matte, smooth.

*Color, mature foliage*.—Upper Leaf Surface: Green Group 137A. Lower Leaf Surface: Green Group 137B.

*Color, juvenile foliage*.—Upper Leaf Surface: Green Group 137A. Lower Leaf Surface: Green Group 138B.

*Anthocyanin intonation*.—Present. Intonations present on margin of juvenile leaves: Greyed-Purple Group 183A.

Stipules:

*Size*.—11-12 mm long.

*Stipule color*.—Margins: Green Group 138A. Base: Yellow-Green Group 145B and 145C.

*Anthocyanin*.—Greyed Red Group 182A on juvenile stipules.

*Stipitate glands*.—On underside of stipules and margins.

*Shape*.—Apex: Apiculate Base: Wedged.

Petiole:

*Length*.—Average 7-15 mm.

*Diameter*.—Average 1 mm.

*Petiole color*.—Green Group 138A. Anthocyanin present on juvenile tissue: Greyed Red Group 183A.

*Underneath*.—Yellow-Green Group 147C.

*Prickles*.—Occasional prickles found on underside.

*Stipitate glands*.—Present on underside and margins.

Petiole rachis:

*Length*.—Average 33 mm.

*Diameter*.—Average 1 mm.

*Color*.—Green Group 138A, with Yellow-Green Group 147C on underside. Anthocyanin present along upper margins, Greyed-Purple Group 183A.

*Margins*.—With stipitate glands.

*Underneath*.—Occasional prickles and light pubescence.

Leaflets:

*Size*.—Average size of the terminal leaflet is 35 mm (l)×20 mm (w).

*Shape*.—Ovate. Base: Obtuse. Apex: Acute.

*Margins*.—Finely serrated.

*Surface*.—Upper: Semi-glossy. Lower: Matte finish.

*Texture*.—Leathery.

*Arrangement*.—Odd pinnate.

*Venation*.—Reticulate.

Hips/seed formation: None observed.

Winter hardiness: Unknown.

Disease resistance: Very good resistance to Powdery mildew (*Sphaerotheca pannosa*) and Botrytis (*Botrytis cinerea*) diseases under normal growing conditions.

I claim:

1. A new and distinct variety of rose plant, as described and illustrated herein.

* * * * *

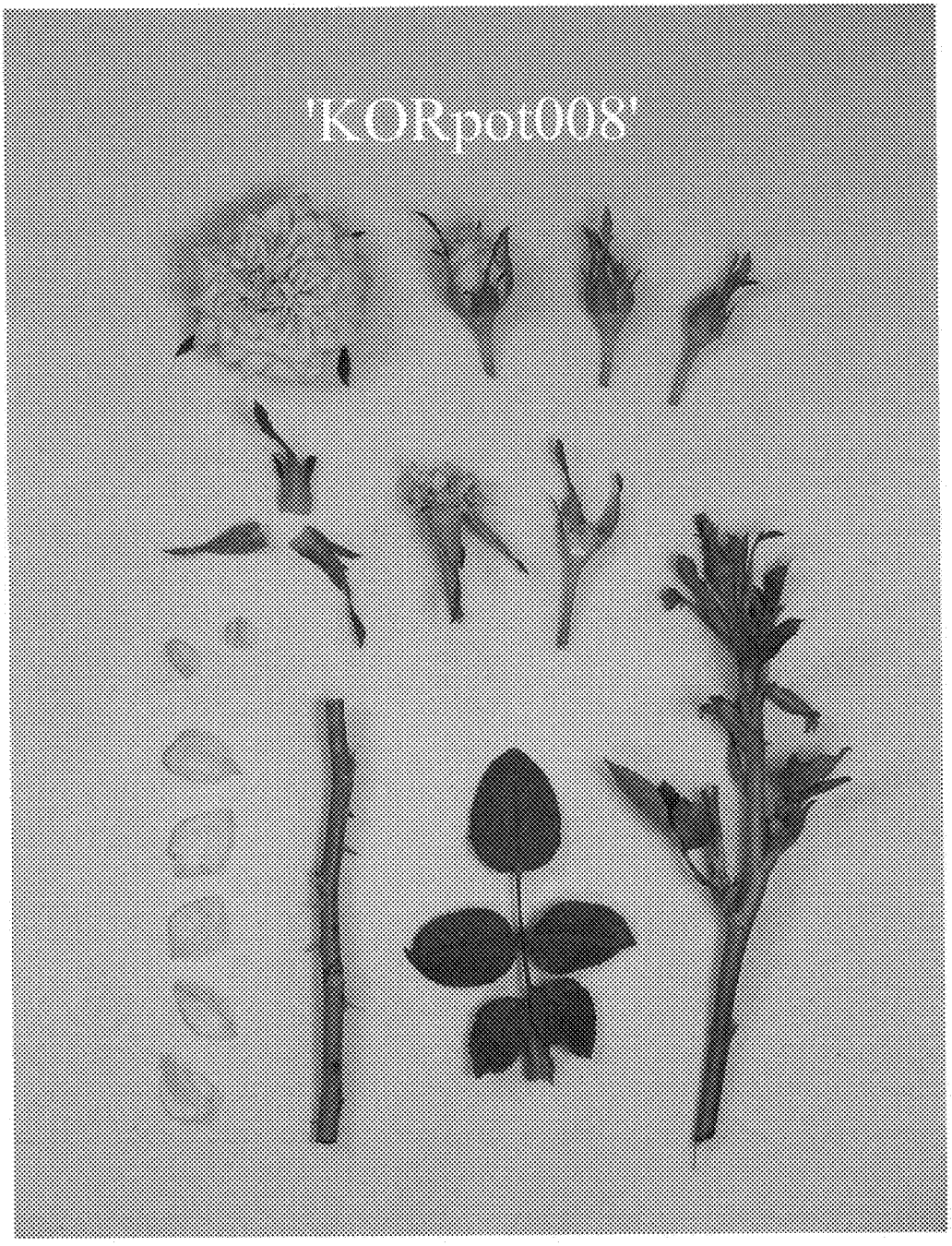
'KORpot008'